(12) United States Patent
Kofidis (10) Patent No.: US 10,709,560 B2
(45) Date of Patent: Jul. 14, 2020

(54) NATURALLY DESIGNED MITRAL PROSTHESIS

(71) Applicant: NATIONAL UNIVERSITY OF SINGAPORE, Singapore (SG)

(72) Inventor: Theodoros Kofidis, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/766,377

(22) PCT Filed: Oct. 10, 2016

(86) PCT No.: PCT/SG2016/050498
§ 371 (c)(1),
(2) Date: Apr. 6, 2018

(87) PCT Pub. No.: WO2017/061956
PCT Pub. Date: Apr. 13, 2017

(65) Prior Publication Data
US 2018/0289484 A1    Oct. 11, 2018

Related U.S. Application Data

(60) Provisional application No. 62/239,036, filed on Oct. 8, 2015.

(51) Int. Cl.
*A61F 2/24* (2006.01)
(52) U.S. Cl.
CPC .............. *A61F 2/2457* (2013.01); *A61F 2/24* (2013.01); *A61F 2/2412* (2013.01); *A61F 2220/0075* (2013.01)

(58) Field of Classification Search
CPC ........ A61F 2/2454; A61F 2/2457; A61F 2/24; A61F 2/2418; A61F 2/30942
See application file for complete search history.

(56) References Cited

U.S. PATENT DOCUMENTS 4,178,639 A    12/1979  Bokros
5,178,632 A     1/1993  Hanson
(Continued)

FOREIGN PATENT DOCUMENTS

SG    D2003118 A    5/2003
WO    1997020524 A1  6/1997
(Continued)

OTHER PUBLICATIONS

Sachweh, Joerg S, et al, Novel "biomechanical" polymeric valve prostheses with special design for aortic and mitral position: a future option for pediatric patients?, ASAIO Journal, 2006, 52(5), 575-580.
(Continued)

*Primary Examiner* — Suba Ganesan
(74) *Attorney, Agent, or Firm* — Soroker Agmon Nordman Pte Ltd (57) ABSTRACT

A prosthetic mitral valve designed to resemble a patient's nat-ural mitral valve is provided. The prosthetic mitral valve includes an asym-metrical, flexible ring dimensioned to match a native mitral annulus of a pa-tient, two leaflets suspended from the flexible ring, and at least two sets of cords attached to the leaflets and merging into two bundles to be fabricated using pre-operative three-dimensional imaging technologies.

20 Claims, 5 Drawing Sheets

(56) References Cited

U.S. PATENT DOCUMENTS

| | | | |
|---|---|---|---|
| 5,415,667 A | 5/1995 | Frater | |
| 5,662,704 A * | 9/1997 | Gross | A61F 2/2412 623/2.1 |
| 5,910,169 A | 6/1999 | Peredo | |
| 6,074,417 A | 6/2000 | Peredo | |
| 6,358,277 B1 | 3/2002 | Duran | |
| 9,155,617 B2 | 10/2015 | Carpentier et al. | |
| 10,080,659 B1 * | 9/2018 | Zentgraf | A61F 2/2457 |
| 2002/0173843 A1 * | 11/2002 | Peredo | A61F 2/2412 623/2.16 |
| 2004/0122512 A1 | 6/2004 | Navia et al. | |
| 2005/0075727 A1 * | 4/2005 | Wheatley | A61F 2/2412 623/2.17 |
| 2007/0050021 A1 | 3/2007 | Johnson | |
| 2010/0023117 A1 * | 1/2010 | Yoganathan | A61F 2/2445 623/2.11 |
| 2013/0053951 A1 | 2/2013 | Ruyra Baliarda | |
| 2014/0052285 A1 | 2/2014 | Butcher et al. | |
| 2014/0058503 A1 | 2/2014 | Umezu et al. | |
| 2015/0335427 A1 | 11/2015 | Zeitani | |
| 2016/0030176 A1 * | 2/2016 | Mohl | A61F 2/2466 623/2.11 |
| 2016/0038246 A1 * | 2/2016 | Wang | G06T 7/73 600/429 |

FOREIGN PATENT DOCUMENTS

| | | |
|---|---|---|
| WO | 2002024119 | 3/2002 |
| WO | 2003037227 A2 | 5/2003 |
| WO | 2004032724 A2 | 4/2004 |

OTHER PUBLICATIONS

David Wheatley et al, Mitral valve replacement with mechanical or bioprosthetic valve, Multimedia Manual of Cardio—Thorasic Surgery, 2005, 2005(0425).

Pooja Singha et al, Bioprosthetic heart valves: impact of implantation on biomaterials, ISRN Biomaterials, 2013, 2013, 1-14.

Peter Bloomfield, Choice of heart valve prosthesis, Heart, 2002, 87(6), 583-589.

Morten O. Jensen et al, The Unsaddled Annulus; Biomechanical Culprit in Mitral Valve Prolapse?, Circulation, 2013, 127, 766-768.

Vahe C Gasparyan, et al, Total Reconstruction of the Mitral Valve with Autopericadium Anatomical Study, Asian Cardiovascular & Thoracic Annals, 2002, 10(2), 137-140.

Bozkurt S, et al, Design, analysis and testing of a novel mitral valve for transcatheter implantation, Annals of Biomedical Engineering, 2017, 45(8), 1852-1864.

Johan van der Merwe, et al, Mitral Valve Replacement—Current and Future Perspectives, Open Journal of Cardiovascular Surgery, 2017, 9, 1-6.

Ahmad Falahatpisheh, et al, Effect of the mitral valve's anterior leaflet on axisymmetry of transmitral vortex ring, Annals of Biomedical Engineering, 2015.

M. Vukićević, et al, Experimental study of an asymmetric heart valve prototype, European Journal of Mechanics B/ Fluids, 2012, 35, 54-60.

* cited by examiner

NATURALLY DESIGNED MITRAL PROSTHESIS

RELATED APPLICATION

This application claims the benefit of U.S. Provisional Application No. 62/239,036, filed on Oct. 8, 2015. The entire teachings of the above application are incorporated herein by reference.

BACKGROUND OF THE INVENTION

Currently available mitral valve prostheses are typically built in an unnatural, circular-shaped manner and are often made of rigid materials. They also often feature three symmetric leaflets, whereas a natural human mitral valve includes only two leaflets, a larger anterior leaflet and a smaller posterior leaflet. Due to their rigid and unnatural construction, such mitral valve prostheses distort the natural anatomy of the heart. The heart muscle surrounding these prostheses does not recover well following implant surgery. The prostheses last an average of only 7-10 years, causing patients to require second and, sometimes, third surgeries during their life span, which repeatedly exposes patients to the high risks of open heart surgery.

SUMMARY OF THE INVENTION

A prosthetic valve designed to resemble a patient's natural mitral valve is provided. Two flexible leaflets and an asymmetric and flexible ring can move with the natural distortion of the heart muscle during a cardiac cycle. Cords, similar to the native chordae tendineae of the patient, are included in the prosthetic valve to mimic the natural prevention of backflow of blood into the atria and to provide support to the left ventricle during systole.

A mitral valve prosthesis includes an asymmetrical ring dimensioned to mimic a native mitral annulus of a patient, two leaflets suspended from the flexible ring and configured to coapt with each other, and at least two sets of cords. Each set of cords can be attached to a leaflet on a first end and merge into a bundle on a second end. The flexible ring, leaflets, and cords create an orifice through which blood flows in one direction.

A method includes fabricating a mitral valve prosthesis including a flexible ring with dimensions mimicking measured dimensions of a native mitral annulus of a patient, two leaflets having dimensions mimicking measured dimensions of native leaflets of the patient, and at least two sets of cords having dimensions mimicking measured dimensions of native chordae tindinae of the patient. The dimensions of the ring, leaflets and cords can be obtained from imaging technologies such as three-dimensional echocardiography, computerized tomography (CT), and magnetic resonance imaging (MRI). The two leaflets are suspended from the flexible ring and configured to coapt with each other. Each set of cords is attached to a leaflet on a first end and merges into a bundle on the second end.

BRIEF DESCRIPTION OF THE DRAWINGS

FIG. 1A depicts a prosthetic mitral valve in an open position and shows chordae prior to attachment to the leaflets. FIG. 1B depicts a prosthetic mitral valve in a closed position and shows chordae following attachment to the leaflets.

FIG. 2 is a schematic of an embodiment of the present invention implanted into the heart.

FIG. 3 is an image of a 3D reconstruction of a mitral valve area in 3D CT image analysis software.

FIG. 4 is a photograph of a 3D printed valve mold and porcine pericardial mitral valve leaflets.

FIG. 5 is a photograph of a prosthetic valve under ex vivo testing.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

A human mitral valve is located between the left atrium and left ventricle of the heart and includes two leaflets, the anterior leaflet and the posterior leaflet. The leaflets coapt to close the mitral valve during systole. Both leaflets are connected to the papillary muscles of the left ventricle by chordae tendineae.

Biological and mechanical mitral valve prostheses are available commercially. In contrast to the soft tissue and asymmetrical shape of the human mitral valve, both biological prostheses and mechanical prostheses have rigid, circular shapes. An additional disadvantage of mechanical valves is that blood has a tendency to clot on the mechanical components of the valve and cause the valve to function abnormally. Patients with mechanical valves must take anticoagulants to prevent the risk of blood clots forming on the valve, which can cause a stroke. Biological valves carry a reduced risk of forming blood clots but have more limited durability as compared with mechanical valves and require more frequent replacement.

Other forms of atrioventricular valves, including mitral valves, are disclosed in U.S. Pat. No. 6,358,277 and in which a template of membrane material is sutured onto the patient's mitral annulus. Such valves feature a high and unnaturally shaped annulus, making the circumference of the prosthetic valve bulky and raised like a collar. Moreover, templates are provided in standard sizes which must then be trimmed to adapt to a patient.

Figure 1A:
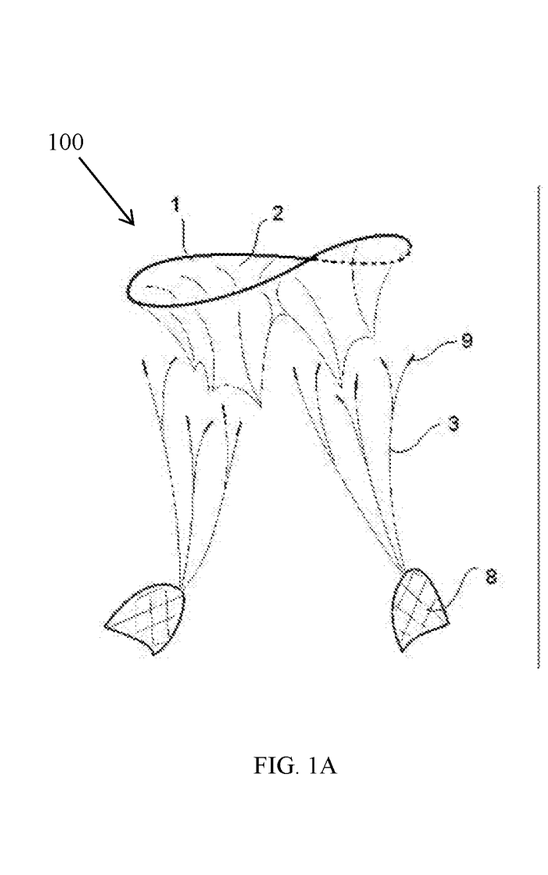
FIGS. 1A and 1B are schematics of embodiments of the present invention.
Figure 1B:
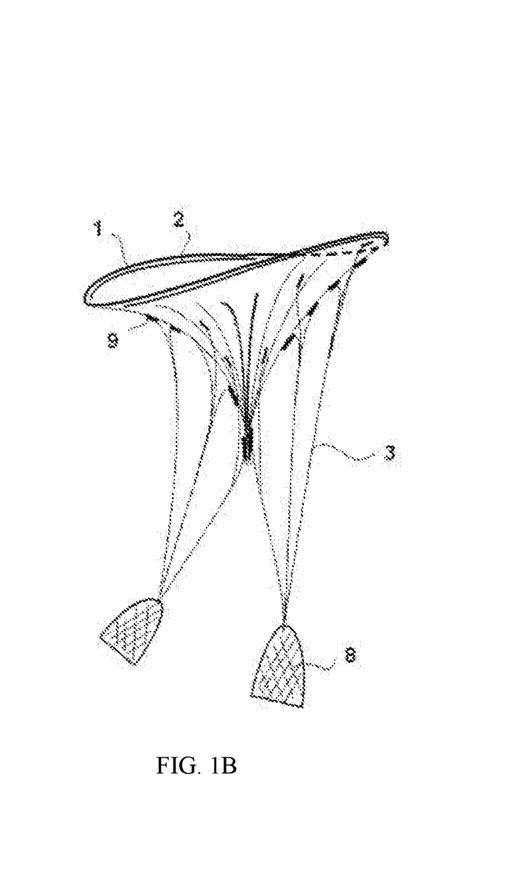

A mitral valve prosthesis of the invention is shown in FIGS. 1A and 1B. The mitral valve prosthesis 100 has a physiological shape that is similar to a natural human mitral valve. The mitral valve prosthesis includes a flexible, asymmetrical ring 1 and two flexible, membrane-like leaflets 2 that are suspended from the asymmetrical ring 1. The mitral valve prosthesis also includes two sets of cords 3 which mimic the chordae tendineae of the heart. Each set of cords 3 is configured to be attached to the margins and/or the bodies of the leaflets 2 at one end, and converge into a fixation cap 8 on the other end. Fixation caps 8 are configured to be sutured on to the papillary muscles of the left ventricle.

The mitral valve 100 is shown with the cords 3 unattached to the leaflets 2 in FIG. 1A and attached in FIG. 1B. The cords 3 may be attached to the leaflets 2 before surgery, or they may be attached during surgery. For example, attachments 9 between cords 3 and leaflets 2 may be sutures or they may be en-block engineered. Mitral valve 100 is shown in an open state in FIG. 1A and a closed state in FIG. 1B. In the closed state, leaflets 2 are shown to coapt.

Figure 2:
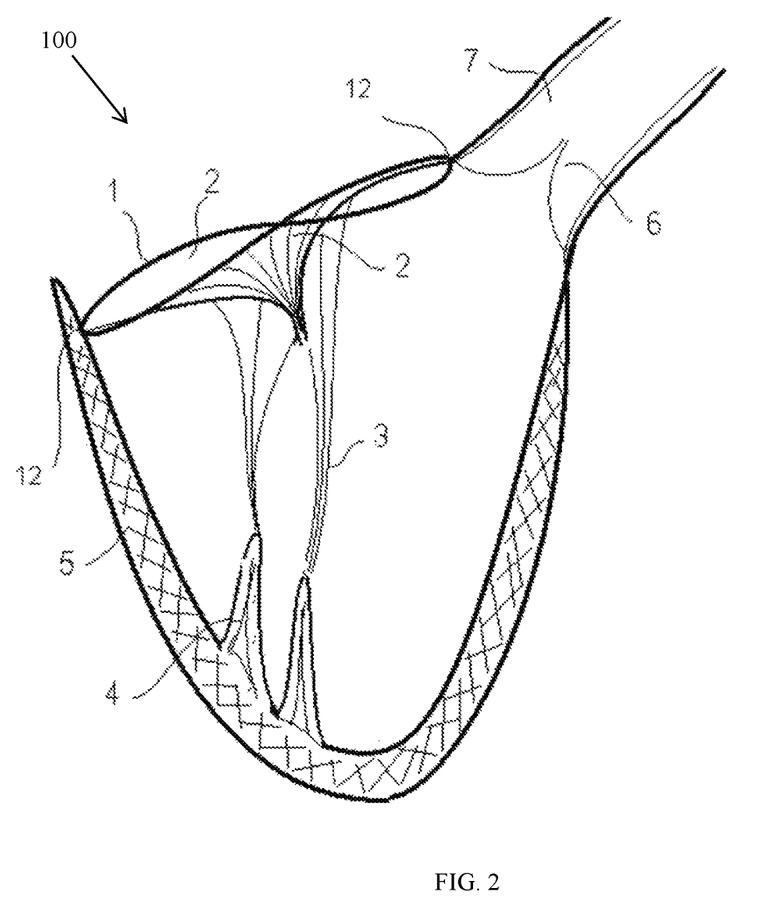

FIG. 2 illustrates mitral valve 100 implanted into the heart. The mitral valve 100 is shown implanted at the location of the native mitral annulus 12, with one side adjacent to the aortic valve 6, where the root of the aorta 7 connects with the left ventricle, and the other side against the opposing ventricular wall 5. Cords 3 are shown attached to the papillary muscles 4.

Flexible ring 1 can be custom-made following an ultrasound examination of a patient's heart. In particular, a three-dimensional echocardiography study can be performed to obtain detailed anatomical measurements and/or render a three dimensional model of the patient's heart from which a customized mitral valve can be produced. Leaflets 2 and cords 3 can also be customized based upon ultrasound imaging of the subject's native mitral valve and surrounding anatomy. Customized mitral valves can also be produced from data obtained by other imaging modalities which provide three-dimensional information, including cardiac CT and cardiac MRI. As such, mitral valve prostheses of the present invention can be selected or designed to match the patient's specific anatomy.

Flexible ring 1 can be formed from, for example, an elastic annuloplasty ring. Leaflets 2 can be formed from natural material or biocompatible composite material which can resist clotting and function similarly to a patient's native anterior and posterior leaflets. At least two sets of cords, attaching to one of the two leaflets on a first end and to the papillary muscles on a second end, are provided to function similarly to the patient's native chordae tendineae. Cords 3, tethering the leaflets 2 to the papillary muscles of the patient, provide support to the left ventricular wall throughout the cardiac cycle and prevent the leaflets from opening into the atrium cavity.

The mitral valve prosthesis 100, including the flexible ring 1, leaflets 2, and cords 3, appears and behaves similar to a healthy, native mitral valve. Additionally, mitral valve prostheses of the present invention can be produced with natural materials and can avoid the inclusion of foreign material, such as pledgets. Homograft material and/or composite material, including various combinations of homograft, xenograft and/or autograft material, can be used to fabricate the flexible ring, leaflets, cords, and caps. The material which forms the valve ring and the leaflets can include, but is not limited to, human, bovine or porcine pericardium, decellularized bioprosthetic material, woven biodegradable polymers incorporated with cells, and extracellular materials. Biodegradable natural polymers can include, but are not limited tofibrin, collagen, chitosan, gelatin, hyaluronan, and similar materials thereof. A biodegradable synthetic polymer scaffold that can be infiltrated with cells and extracellular matrix materials can include, but is not limited to, poly(L-lactide), polyglycolide, poly(lactic-co-glycolic acid), poly(caprolactone), polyorthoesters, poly(dioxanone), poly(anhydrides), poly(trimethylene carbonate), polyphosphazenes, and similar materials thereof. Flexible rings can be further customized to provide individualized flexibility or rigidity for the patient. Additionally, some components of the mitral valve prosthesis, including cords 3, can be fashioned intraoperatively by autologous pericardium of the patient.

For example, a mitral valve prosthesis can be fabricated from the patient's own pericardium. Alternatively, the mitral valve prosthesis can be fabricated from xenogeneic materials (e.g., animal tissues, such as existing valves) over which a layer of the patient's own cultured cells is applied by means of tissue engineering.

Artificial valves are frequently fixed with glutaraldehyde, which is a known toxin and promotes regeneration. Mitral valve prostheses of the present invention can be fixed by non-glutaraldehyde-based methods, such as dye-mediated photofixation. Mitral valves of the present invention can also be fixed by using alternative cross-linking agents, such as epoxy compounds, carbodiimide, diglycidyl, reuterin, genipin, diphenylphosphorylazide, acyl azides, and cyanamide, or by physical methods, such as ultraviolet light and dehydration.

Mitral valve prostheses, or some components of the prostheses, can be produced directly with biological three-dimensional (3D) printing using biological materials. Alternatively, mitral valve prostheses, or some components of the prostheses, can be produced using a template or mold constructed by three-dimensional printing, based on the detailed dimensions obtained from three-dimensional imaging performed pre-operatively.

A method of implanting a mitral valve prosthesis is also provided. Prior to implantation, an echocardiography study (or other imaging study) of the patient is obtained. From the imaging study, heart chamber sizes and movements are measured. The detailed dimensions of the patient's mitral annulus, leaflets and cords are also measured from the acquired images. Additionally, a three-dimensional depiction of the valve to be replaced can be rendered. From the measurements and three-dimensional modeling of the patient's native valve, a mitral valve prosthesis can be produced that closely matches the patient's native mitral valve corrected for the existing pathology.

A three dimensional echocardiography study can be performed with, for example, a transesophageal echocardiography (TEE) probe or a transthoracic echocardiography (TTE) probe. Segments of the mitral valve can be three-dimensionally and four-dimensionally modelled and measured using software such as eSieValves™ (Siemens Medical Solutions USA, Inc., Malvern, Pa.). Relevant measurements can include outer and inner diameters of the annulus, annular areas, intertrigonal and intercomm distances, and lengths along various axes of the anterior and posterior leaflets.

Figure 3:
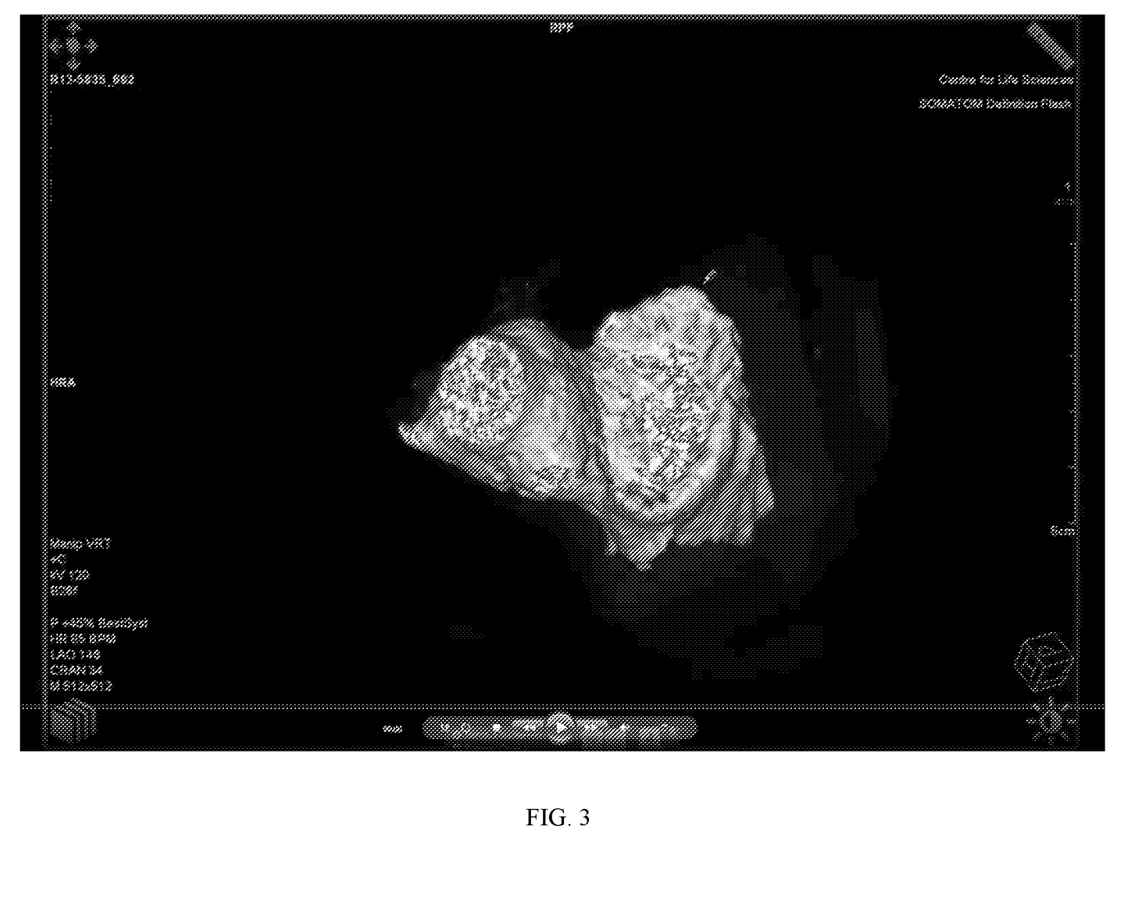

In addition, or alternatively, a three dimensional study of a mitral valve can be performed with computed tomography (CT) or magnetic resonance imaging (MRI). For example, as shown in FIG. 3, a 3D reconstruction of a porcine heart was obtained using CT imaging (SOMATOM® Definition Flash, Siemens Healthcare, Erlangen, Germany), with the mitral valve area of the heart visible on the right side of the image. Segmentation of the mitral valve area can be performed using the image analysis software and relevant measurements can be obtained.

Figure 4:
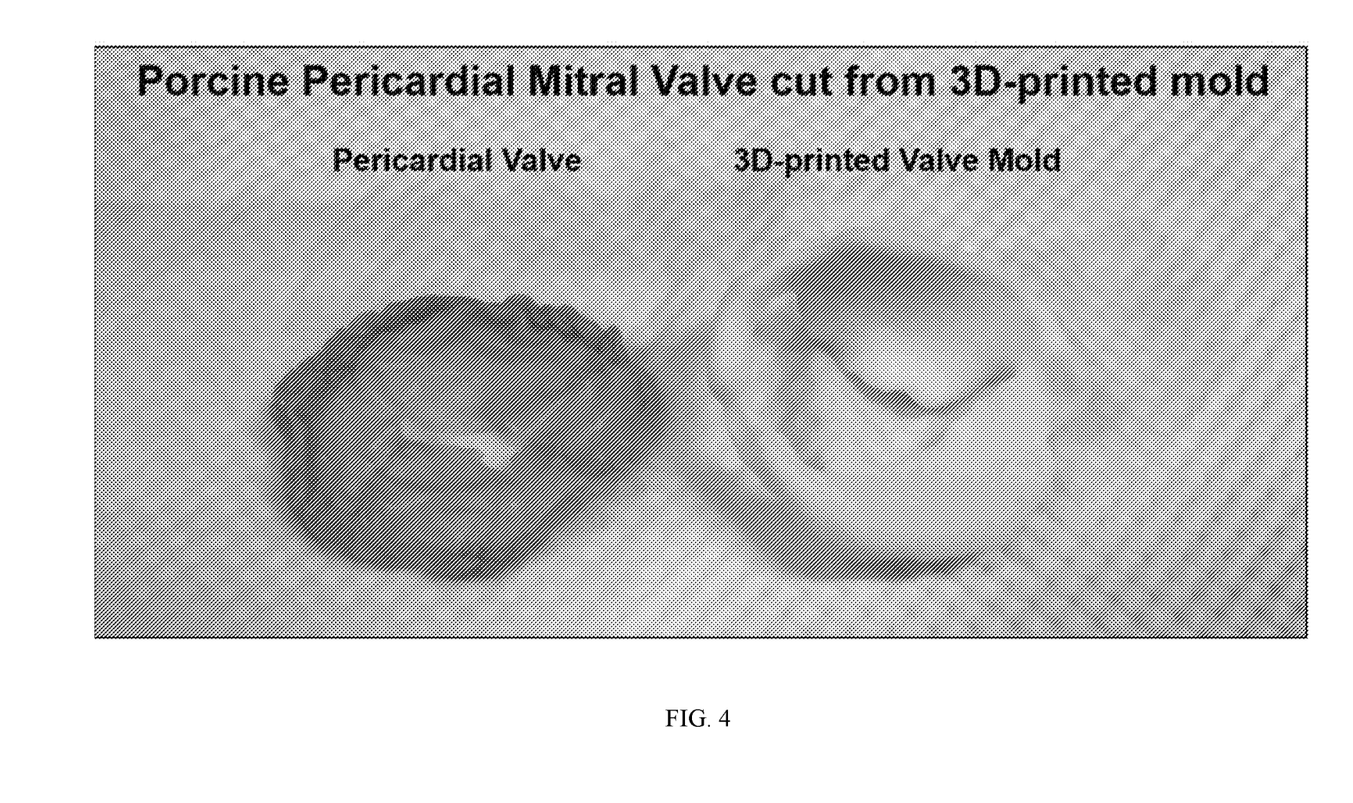

The mitral valve prosthesis can be completely customized for a patient, with each component (e.g., ring, leaflets, cords, caps) fabricated to have dimensions that match those of the patient's native valve. For example, as shown in FIG. 4, a 3D printed mold of a mitral valve was created based on a 3D reconstruction of an imaged valve. The 3D printed valve shown in FIG. 4 was modeled during the diastolic, or opening, phase of the cardiac cycle. A prosthetic valve based on the 3D mold is also shown in FIG. 4. The mold can guide the cutting of porcine pericardium into leaflets and chordae attachment sites. Alternatively, a prefabricated mitral valve, or prefabricated components of a mitral valve, can be selected for implantation that are closest in shape and size to the patient's native valve or native valve components.

Figure 5:
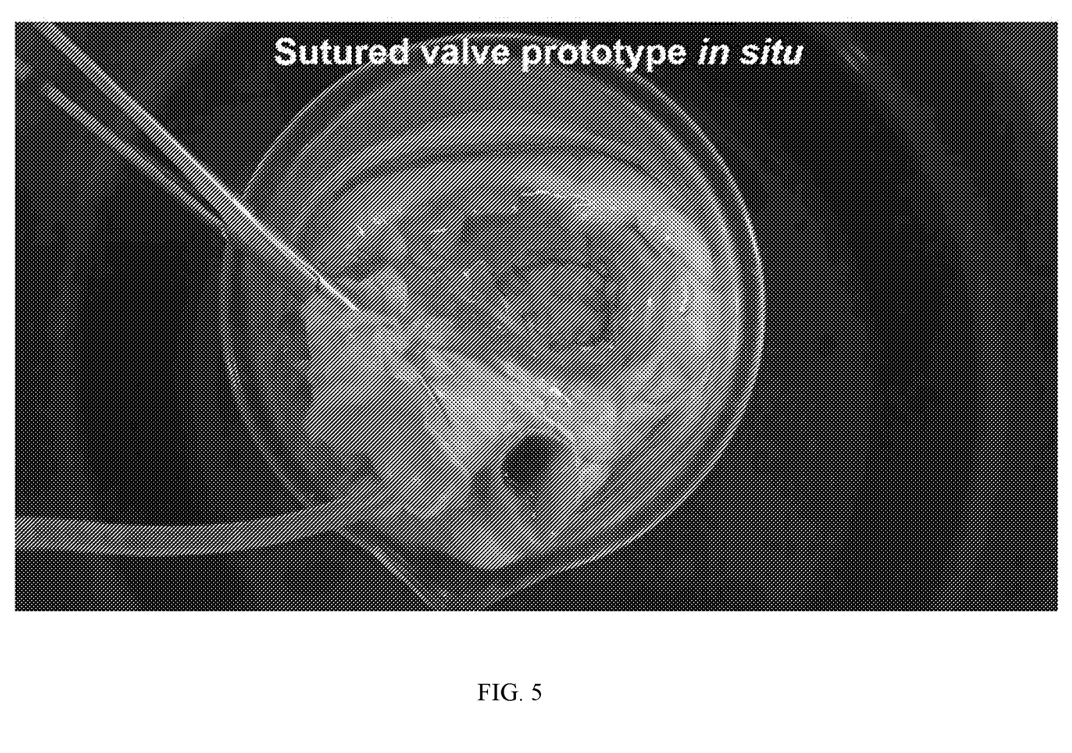

FIG. 5 shows an image of a prosthetic valve prototype sutured in an ex vivo testing system. The valve prototype is shown sutured to an explanted whole heart. Saline boluses are injected through a tube into the left ventricle of the heart with the aorta clamped to contain the saline in the left ventricle and to create pressure. The injection pressure can be monitored, for example, on a pressure gauge connected to the injection line. The competency of the valve prototype (e.g., absence of regurgitation and prolapse of the valve leaflets) under physiological pressure can then be monitored. Competency of the valve can be measured or monitored while the left ventricle is contracting and at the systolic pressure at which a native valve closes.

In preparation for implantation to a patient, the heart of the patient is arrested, as is usual for mitral valve surgeries. During implantation, the flexible ring of the prosthesis is affixed by sutures to the native annulus and the papillary caps are sutured to the native papillary muscles. For example, two sutures can be applied at the tip of each of the native papillary muscles, affixing a cap to the muscle. The clinician ensures that the valve will open and close completely by filling the ventricular chamber with a physiological saline under an appropriate pressure and checking the motion and the competence of the replaced valve as it closes due to the exerted pressure. Following implantation, the valve is examined with transesophageal echocardiography (TEE) after the heart is closed and has resumed beating.

If necessary, the subject can be placed on anticoagulation medication following implantation. Given the natural shape and natural materials used to construct mitral valve prostheses of the present invention, low doses of anticoagulation medication or no anticoagulation medication, is expected for most patients.

The currently available biological and mechanical prostheses carry several disadvantages: they contain bulky foreign material, require strong anticoagulation medication, have short useful lives requiring the patient to undergo subsequent surgeries when they must be replaced, and do not assist the heart in recovering efficiently from implantation. The present invention offers several advantages over the biological and mechanical prostheses described above. Having a design that more closely matches the native mitral valve of a patient and being fabricated from natural materials, the mitral valve prostheses described are expected to require less recovery time for the patient, provide a longer useful life, and alleviate or omit the need for anticoagulant medication.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A mitral valve prosthesis, comprising:
   an asymmetrical, flexible ring, the ring dimensioned to mimic a native mitral annulus of a patient;
   two leaflets suspended from the flexible ring and configured to coapt with each other;
   at least two sets of cords, each set of cords attached to a leaflet on a first end and merging into a bundle on a second end; and
   two caps configured to attach to papillary muscles of the patient, each bundle of cords merging into one of the two caps, such that each bundle of cords is connected to the papillary muscles of the patient via one of the two caps,
   the flexible ring, leaflets, cords and caps creating an orifice through which blood flows in one direction
   wherein dimensions of the flexible ring, leaflets, cords and caps match imaged dimensions of 3D imaging of a native mitral valve of a heart of the patient;
   and further wherein at least one of said flexible ring, leaflets, cords and caps are fabricated from autologous pericardium of the patient.

2. The mitral valve prosthesis of claim 1 wherein one of the two leaflets is dimensioned to mimic a native anterior leaflet of the patient and the other of the two leaflets is dimensioned to mimic a native posterior leaflet of the patient.

3. The mitral valve prosthesis of claim 1 wherein the cords are dimensioned to mimic native chordae tendineae of the patient.

4. The mitral valve prosthesis of claim 1 wherein dimensions of the flexible ring are obtained from a three-dimensional imaging study of the patient.

5. The mitral valve prosthesis of claim 1 wherein dimensions of the leaflets are obtained from a three-dimensional imaging study of the patient.

6. The mitral vale prosthesis of claim 1 wherein dimensions of the cords are obtained from a three-dimensional imaging study of the patient.

7. The mitral valve prosthesis of claim 1 wherein the flexible ring is fabricated with biological three-dimensional printing.

8. The mitral valve prosthesis of claim 1 wherein the flexible ring and leaflets are fabricated with homograft material.

9. The mitral valve prosthesis of claim 1 wherein the flexible ring and leaflets are fabricated with biocompatible composite material.

10. The mitral valve prosthesis of claim 1 wherein a rigidity of the flexible ring is customised for the patient.

11. The mitral valve prosthesis of claim 1, wherein each of said two caps are attached to the papillary muscles via sutures.

12. The mitral valve prosthesis of claim 1, wherein the cords and caps are fabricated with homograft material.

13. The mitral valve prosthesis of claim 1, wherein each of the at least two sets of cords is sutured to each of the two leaflets.

14. A method comprising:
   performing 3D imaging of a native mitral valve of a heart of a patient;
   obtaining dimensions of a ring, two leaflets, cords and caps of the native mitral valve based on the 3D imaging; and
   fabricating a mitral valve prosthesis according to said dimensions, the mitral valve prosthesis including:
   a flexible ring with dimensions mimicking measured dimensions of a native mitral annulus of the patient,
   two leaflets suspended from the flexible ring and having dimensions mimicking measured dimensions of native leaflets of the patient, the two leaflets configured to coapt with each other,
   at least two sets of chords, each set of cords attached to a leaflet on a first end and merging into a bundle on the second end, the cords having dimensions mimicking measured dimensions of native chordae tendineae of the patient, and two caps configured to attach to papillary muscles of the patient, each bundle of cords merging into one of the two caps, such that each bundle of cords is connected to the papillary muscles of the patient via one of the two caps;

wherein at least one of said flexible ring, leaflets, cords and caps are fabricated from autologous pericardium of the patient.

15. The method of claim 14 wherein the measured dimensions of the native mitral annulus, native leaflets, and native chordae tendineae are obtained from an imaging study conducted on the patient.

16. The method of claim 15, wherein the imaging study is a three-dimensional imaging study.

17. The method of claim 12 wherein the flexible ring and leaflets are fabricated with homograft material.

18. The method of claim 14 wherein the flexible ring and leaflets are fabricated with biocompatible composite material.

19. The method of claim 14 wherein the fabricating includes printing at least one of the flexible ring, leaflets, and cords with three-dimensional biological printing.

20. The method of claim 14, wherein the cords and caps are fabricated with homograft material.

* * * * *

UNITED STATES PATENT AND TRADEMARK OFFICE
CERTIFICATE OF CORRECTION

PATENT NO. : 10,709,560 B2
APPLICATION NO. : 15/766377
DATED : July 14, 2020
INVENTOR(S) : Theodoros Kofidis Page 1 of 1

It is certified that error appears in the above-identified patent and that said Letters Patent is hereby corrected as shown below:

In the Claims

Column 7, Line 18, In Claim 17:
Delete "The method of claim 12" and insert --"The method of claim 14"--.

Signed and Sealed this
Tenth Day of November, 2020

Andrei Iancu
*Director of the United States Patent and Trademark Office*